United States Patent
Sawan et al.

(10) Patent No.: US 6,180,584 B1
(45) Date of Patent: Jan. 30, 2001

(54) DISINFECTANT COMPOSITION PROVIDING SUSTAINED RESIDUAL BIOCIDAL ACTION

(75) Inventors: Samuel P. Sawan, Tyngsboro; Sundar Subramanyam, Stoneham; Alexander Yurkovetskiy, Acton, all of MA (US)

(73) Assignee: Surfacine Development Company, LLC, Tyngsboro, MA (US)

( * ) Notice: Under 35 U.S.C. 154(b), the term of this patent shall be extended for 0 days.

(21) Appl. No.: 09/248,861

(22) Filed: Feb. 11, 1999

Related U.S. Application Data (60) Provisional application No. 60/074,456, filed on Feb. 12, 1998.

(51) Int. Cl.⁷ .................... C11D 3/48; C11D 3/12; C11D 3/30

(52) U.S. Cl. ............ 510/382; 510/131; 510/214; 510/238; 510/383; 510/385; 510/386; 510/390; 510/499

(58) Field of Search .................... 510/130, 131, 510/140, 157, 214, 238, 382, 383, 385, 386, 390, 405, 406, 412, 414, 426, 427, 499

(56) References Cited

U.S. PATENT DOCUMENTS

| 3,050,467 | 8/1962 | Horowitz et al. ............. 252/107 |
| 4,055,655 | 10/1977 | Maurer et al. ............. 424/294 |
| 4,165,334 | * 8/1979 | Gosselink et al. ............. 260/458 R |

(List continued on next page.)

FOREIGN PATENT DOCUMENTS

| 0 328 421 | 8/1989 | (EP) | ............. A61L/29/00 |
| 328 421 A2 | 8/1989 | (EP) | ............. A61L/29/00 |
| 0 588 601 A1 | 3/1994 | (EP) | ............. C07F/7/18 |
| 0 639 636 A2 | 2/1995 | (EP) | ............. C11D/3/48 |
| 2 122 900 | 1/1984 | (GB) | ............. A01N/31/02 |
| 58 200884 | 11/1983 | (JP) | ............. C08K/3/16 |
| 61-8104 | 1/1986 | (JP) | ............. B01D/13/00 |
| 2-68105 | 3/1990 | (JP) | ............. B01D/38/14 |
| 63-218558 | 3/1990 | (JP) | ............. B01D/38/14 |
| 2-192937 | 7/1990 | (JP) | ............. B32B/15/08 |
| 3065223 | 3/1991 | (JP) | ............. B01D/69/00 |
| 4-197362 | 7/1992 | (JP) | ............. A61M/25/00 |
| 4-197363 | 7/1992 | (JP) | ............. A61M/25/00 |
| 4-70935 | 11/1992 | (JP) | ............. G06F/11/32 |
| 5033217 | 2/1993 | (JP) | ............. D01F/6/94 |
| 90 04390 | 5/1990 | (WO) | ............. A61K/31/155 |
| WO 90/04390 | 5/1990 | (WO) | ............. A61K/31/155 |
| WO93/22320 | 11/1993 | (WO) | ............. C07F/9/09 |
| WO 95/17152 | 6/1995 | (WO) | ............. A61J/1/14 |
| WO 98/18330 | 5/1998 | (WO) | ............. A01N/59/16 |

OTHER PUBLICATIONS

Chemical Abstracts, vol. 127, No. 14 (Oct. 6, 1997).
Davis et al., "Electrode and Bacterial Survival with Iontophoresis in Synthetic Urine", *J. Urology*, 147:1310–1313 (1992).
Pyle et al., "Efficacy of Copper and Silver Ions with Iodine in the Inactivation of *Pseudomonas cepacia*", *J. Appl. Bact.*, 72:71–79 (1992).
Quesnel et al., "Synergism Between Chlorhexidine and Sulphadiazine," *J. Appl. Bact.*, 45:397–405 (1978).
Williams et al., "The Biocompatability of Silver", *CRC Crit. Rev. Biocompat.*, 5(3):221–243 (1989).

*Primary Examiner*—Yogendra Gupta
*Assistant Examiner*—Christine Ingersoll
(74) *Attorney, Agent, or Firm*—Testa, Hurwitz & Thibeault, LLP (57) ABSTRACT

The present invention relates to a composition that, when applied to a substrate, forms an adherent, transparent, water insoluble polymeric film on the substrate surface that provides sustained antimicrobial disinfecting action for prolonged periods, without the necessity for reapplication. The coating provides surface disinfecting action by a contact-killing mechanism, and does not release its components into contacting solutions at levels that would result in solution disinfection. The polymeric film formed by the composition of the invention can be removed by treatment with dilute alcoholic base.

38 Claims, 4 Drawing Sheets

U.S. PATENT DOCUMENTS

| | | | |
|---|---|---|---|
| 4,563,485 | 1/1986 | Fox, Jr. et al. | 523/113 |
| 4,581,028 | 4/1986 | Fox, Jr. et al. | 623/2 |
| 4,612,337 | 9/1986 | Fox, Jr. et al. | 523/113 |
| 4,654,208 | 3/1987 | Stockel et al. | 424/78 |
| 4,783,340 | 11/1988 | McDonnell et al. | 427/2 |
| 5,019,096 | 5/1991 | Fox, Jr. et al. | 623/1 |
| 5,061,485 | 10/1991 | Oakes et al. | 424/81 |
| 5,108,643 | 4/1992 | Loth et al. | 252/174.11 |
| 5,142,010 | 8/1992 | Olstein | 526/248 |
| 5,158,766 | 10/1992 | Greenwald et al. | 424/78.33 |
| 5,334,588 | 8/1994 | Fox, Jr. et al. | 514/171 |
| 5,401,327 * | 3/1995 | Elis et al. | 134/42 |
| 5,490,938 * | 2/1996 | Sawan et al. | 210/651 |
| 5,527,506 | 6/1996 | Hamilton | 422/18 |
| 5,529,713 | 6/1996 | Gauthier-Fournier | 252/106 |
| 5,576,006 | 11/1996 | Smith | 424/404 |
| 5,578,563 * | 11/1996 | Trihn et al. | 510/513 |
| 5,585,407 | 12/1996 | Patel et al. | 514/772.6 |
| 5,668,084 | 9/1997 | Unhoch et al. | 504/158 |
| 5,681,468 * | 10/1997 | Sawan et al. | 210/500.25 |
| 5,776,479 * | 7/1998 | Pallos et al. | 424/406 |
| 5,817,325 | 10/1998 | Sawan et al. | 424/411 |
| 5,849,311 | 12/1998 | Sawan et al. | 424/406 |
| 5,869,073 | 2/1999 | Sawan et al. | 424/406 |
| 5,871,763 * | 2/1999 | Luu et al. | 424/402 |
| 5,885,562 * | 3/1999 | Lowry et al. | 424/65 |
| 5,985,931 * | 11/1999 | Modak et al. | 514/634 |
| 6,004,510 * | 12/1999 | Gilbert et al. | 422/29 |
| 6,030,632 * | 2/2000 | Sawan et al. | 424/405 |

* cited by examiner

REPETITIVE CHALLENGE AFTER 3 HR INCUBATION

FIG. 3b

REPETITIVE CHALLENGE AFTER 20 HRS INCUBATION

DISINFECTANT COMPOSITION PROVIDING SUSTAINED RESIDUAL BIOCIDAL ACTION

This application claims benefit of Provisional application Ser. No. 60/074456, filed Feb. 12, 1999.

FIELD OF THE INVENTION

The present invention relates to a composition that forms an adherent, transparent, water insoluble polymeric film on a substrate surface, and that provides sustained antimicrobial disinfecting action upon contact with microorganisms for prolonged periods, without the necessity for reapplication. The coating provides contact-killing surface disinfecting action only, and does not release its components into contacting liquids at levels that would result in solution disinfection. The polymeric film of the invention can be easily removed by treatment with dilute alcoholic base.

BACKGROUND OF THE INVENTION

The constant threat of bacterial contamination and the associated repercussions on health have made antimicrobial solutions a ubiquitous part of commercial and residential cleaning and disinfection processes. Dilute aqueous detergents show no detectable reduction in bacterial levels on surfaces amenable to bacterial growth and proliferation in susceptible environments, such as hospitals and in residential kitchen and bath areas. On the other hand, oxidants such as aqueous hypochlorite and phenolic compositions produce substantial reductions in bacterial levels that are relatively short-lived (3 to 6 hours). This often results in recontamination due to reuse of such surfaces, requiring frequent reapplication of disinfectant. Further, relatively high concentrations of the active agent have to be incorporated in such formulations to obtain broad spectrum disinfection. These high concentrations often have undesirable side effects such as skin and eye irritation, in addition to being potentially hazardous when in contact with food. There is therefore a need for the development of new disinfecting formulations that can provide sustained broad spectrum microbial disinfection on surfaces over prolonged periods without reapplication, even after being contacted by cleaning solutions and after surface reuse. Furthermore, it is desirable to achieve disinfecting action using low levels of the antimicrobial agent that will not pose toxicity problems for the user.

The modality of action of film-forming surface sanitizers to date has been solution based, that is, the antimicrobial action is obtained by controlled release via diffusion or dissolution of the active agents into contacting aqueous or volatile solutions. Numerous examples of this type of sanitizer have been reported. Another typical variant involves hydrolysis or dissolution of the matrix containing an antimicrobial compound, thereby effecting its release into solution. High levels of preservatives, however, are also released into contacting solutions in long-term applications. In such mechanisms, a bioactive compound is covalently bound either directly to the substrate surface or to a polymeric material that forms a nondissolving surface coating. The antimicrobial compounds in such coatings exhibit greatly diminished activity, unless assisted by hydrolytic breakdown of either the bound antimicrobial or the coating itself. In either case, relatively high levels of preservative have to be released into solution in order to elicit antimicrobial action.

SUMMARY OF THE INVENTION

It is an object of the invention to provide an antimicrobial composition which can be applied to a surface to provide a non-leaching, water-insoluble film which is capable of (i) providing immediate antimicrobial disinfection and antiviral action on the surface, and (ii) providing sustained antimicrobial disinfecting action for prolonged periods after application, even after being contacted by water and aqueous surface cleaners. It is also an object of the invention to provide a disinfecting composition that, when applied to a surface, provides a water insoluble film that can be removed from the surface upon application of a non-aqueous, film-dissolving formulation. Another object of the invention is to provide a disinfectant composition which further includes an optical reporter, e.g., a fluorophore or an optical brightening agent that enables detection of the composition on a surface by suitable detection devices such as irradiation by an ultraviolet or visible light source.

The invention further provides disinfecting compositions that form transparent, adherent, water insoluble films which, when applied on a surface, kill microorganisms contacting the films, but which do not leach or elute significant amounts of antimicrobial components or species into the contacting liquids at levels sufficient to provide disinfection in the contacting solution. The antimicrobial composition comprises a combination of an organic biguanide polymer and an antimicrobial metallic material.

More particularly, disinfecting compositions of the invention comprise a liquid, gel or foam comprising a solution, dispersion, emulsion or suspension of a polymeric, film-forming material and a metallic biocide in a carrier, which, when applied to a surface, forms a water-insoluble polymeric film on the surface in which the biocide is non-leachably bound to, complexed with, associated with or dispersed. The polymeric film forming material preferably comprises a polymer, copolymer or adduct which contains segments that, when the polymer forms a film on a surface, are capable of engaging microorganisms that come in contact with it. The biocide preferably is non-leachably attached to, complexed or associated with or dispersed within said film, but is capable of being preferentially transferred directly from the polymeric film to the contacting microorganism due to a higher affinity for proteins within the microorganisms.

In one aspect, the composition comprises a combination of (i) an organic polymeric polycationic material which is capable of forming a layer, film or matrix, and (ii) a broad spectrum metallic biocide which, upon application, becomes intercalated in the layer, film or matrix and that interacts sufficiently strongly with the organic material so that the biocide does not dissolve into or elute from the matrix into the surrounding environment. The organic material should possess two important properties: it should be capable of reversibly binding or complexing with the biocide, and should be capable of insinuating the biocide into the cell membrane of a microorganism in contact with it. The organic material preferably is capable of dissolving into or adhering to the cell membrane surrounding the microorganism. Preferred organic materials are those which can be applied on a surface as water-insoluble films and which bind the biocide in such a manner as to permit transfer of the biocide into the microorganism, but will not release the biocide into the surrounding environment, e.g., into the air or into any liquid in contact with the coated surface.

The biocide preferably is a low molecular weight metallic material that is toxic to microorganisms and is capable of complexing with or reversibly binding to the organic matrix material, thereby rendering the organic matrix water insoluble. The biocide exhibits greater binding affinity for functional groups in cellular proteins of microorganisms.

When a microorganism contacts the antimicrobial material, the organic material engages or disrupts at least the outer portion of the lipid bilayer of the microorganism's cell membrane sufficiently to permit insinuation of the biocide into the microorganism, where cell proteins or proteins in the lipid bilayer compete effectively for the biocide due to favorable binding constants. Stated another way, the metallic material binds to or forms a complex with the organic material in which the association between the organic material and metallic material is sufficiently strong that the layer or film does not elute antimicrobial amounts of the metal into a contacting solution. However, the metallic material preferentially binds to certain proteins in the microorganism and thus is transferred from the matrix to the microorganism. The result is a contact-killing delivery system that selectively transfers the biocide to or into the microorganism's cell membrane upon contact, without elution or dissolution of the biocide into solution, thereby maintaining the long term antimicrobial efficacy of the composition.

The antimicrobial compositions of the present invention are, therefore, molecularly designed to enable a matrix-bound biocide to retain high antimicrobial activity without elution of any compounds into contacting solutions, carriers or other materials. The antimicrobial activity stems from the sustained, cooperative biocidal action of its components. Selective transfer of one component from within the matrix directly to the microorganism upon contact is achieved via a "hand off" mechanism upon engagement and penetration of the microorganism's cell membrane. The antimicrobial material, therefore, maintains long term efficacy without releasing toxic elutables into the surrounding environment.

Organic materials useful in the present invention comprise materials which are capable of: (1) adhering to and/or forming a layer or coating on a variety of substrates, (2) reversibly binding or complexing with the biocide, and (3) insinuating the biocide into the cell membrane of the microorganism upon contact. A preferred class of materials are those having the aforementioned properties, and which are capable of complexing and/or binding a bactericidal metallic material. Most preferred is the class of organic materials having antimicrobial activity. For example, a preferred class of materials, polymeric biguanides, form a layer or coating when applied to a substrate. The layer or coating can dissolve into, or adhere to, and penetrate at least the outer portion of the lipid bilayer membrane of a microorganism. For this purpose, surface active agents, such as cationic compounds, polycationic compounds, anionic compounds, polyanionic compounds, non-ionic compounds, polynonionic compounds or zwitterionic compounds are useful. These compounds include, for example, biguanide polymers, or polymers having side chains containing biguanide moieties or other cationic functional groups, such as benzalkonium groups or quarternium groups (e.g., quarternary amine groups). The polymer backbone may be any polymer capable of forming a coating on a substrate. It is understood that the term "polymer" as used herein includes any organic material comprising three or more repeating units, and includes oligomers, polymers, copolymers, terpolymers, etc. The polymer backbone may be a polysilane or polyethylene polymer, for example. Organic materials which currently are most preferred for use in the invention are polymeric biguanide compounds.

The organic polymeric material may be reacted with a water insoluble organic compound or "hydrophobic agent" in order to increase its water insolubility. In a preferred embodiment, the organic material is a polymeric polycationic polymer, which is chemically reacted with a hydrophobic agent to form an adduct. The adduct that includes the hydrophobic agent adheres more strongly to certain substrates than the polycationic polymer alone, and exhibits greater water insolubility. Hydrophobic agents which can be used in the present invention are organic compounds which are substantially water insoluble and which can react with the polycationic material to form an adduct. Suitable hydrophobic agents include, for example, compounds, which may be polymers, containing organic multifunctional groups such as isocyanates, epoxides, carboxylic acids, acid chlorides, acid anhydrides, succimidyl ether aldehydes, ketones, alkyl methane sulfonates, alkyl trifluoromethane sulfonates, alkyl paratoluene methane sulfonates, alkyl halides and organic multifunctional epoxides. In a currently preferred embodiment, the organic material comprises an adduct of polyhexamethylene biguanide polymer and an epoxide, such as methylene-bis-N,N-diglycidylaniline, bisphenol-A-epichlorohydrin or N-N-diglycidyl-oxyaniline.

The biocidal material can be any antimicrobial material which is capable of non-leachably binding to or complexing with an organic matrix, but which, when placed in contact with the microorganism, preferentially transfers to proteins in the microorganism. For this purpose, metallic materials which bind to cellular proteins of microorganisms and are toxic to the microorganisms are preferred. The metallic material can be a metal, metal oxide, metal salt, metal complex, metal alloy or mixture thereof. Metallic materials which are bactericidal or bacteriostatic and are either substantially water-insoluble or can be rendered water insoluble are preferred. By a metallic material that is bacteriostatic or bactericidal is meant a metallic material that is bacteriostatic to a microorganism, or that is bactericidal to a microorganism, or that is bactericidal to certain microorganisms and bacteriostatic to other microorganisms. Examples of such metals include, silver, zinc, cadmium, lead, mercury, antimony, gold, aluminum, copper, platinum and palladium, their salts, oxides, complexes, and alloys, and mixtures thereof. The appropriate metallic material is chosen based upon the use to which the invention is to be put. The preferred metallic materials are silver compounds. In a currently preferred embodiment, a silver halide is used, most preferably, silver iodide. In another preferred embodiment silver nitrate is used and is converted into a water insoluble silver halide by subsequent chemical reaction with an alkali halide. Most preferably, silver nitrate is converted to silver iodide by reacting it with sodium or potassium iodide.

The invention comprises compositions for forming a non-leaching antimicrobial layer or coating on a surface. In one embodiment, the composition is a sprayable composition comprising a solution, dispersion or suspension of the organic material and the biocidal material. Alternatively, the antimicrobial material can be suspended in water or in aqueous solutions containing an organic solvent in the form of an emulsion, microemulsion, latex or colloidal suspension. The composition need not be a homogeneous solution. If desired, stabilizing agents such as suspending agents or surface active agents may be included. If a more hydrophobic coating or film is desired, the solution, dispersion or suspension also may contain the hydrophobic agent. As a first step, the hydrophobic agent and the organic material may be reacted to form an adduct in which the hydrophobic agent is covalently linked to the organic polymeric material. To form a contact-killing non-leaching coating or layer on a substrate, the disinfectant composition is applied to the substrate, e.g. by wiping, brushing, dipping or spraying, or as an aerosol spray using a suitable propellant, under conditions sufficient to form a layer or film of the polymeric organic material on the substrate.

Liquids useful as a liquid carrier for the antimicrobial materials in the present invention include any polar solvent, including water, alcohols such as ethanol or propanol, polar aprotic solvents such as N,N-dimethyl formamide (DMF), N,N-dimethyl acetamide (DMAC), dimethyl sulfoxide (DMSO), dimethyl sulfide (DMS) or N-methyl-2-pyrrolidone (NMP), and mixtures thereof. The currently preferred liquid carrier comprises a mixture of ethanol and water. In alternative embodiments, the carrier comprises a gel or foam.

In the methods of the invention described above, the amounts and/or concentrations of the materials used will depend upon the nature and stoichiometry of the materials used, and the end product desired. In the currently preferred embodiments, the total solids concentration of the solution, dispersion or suspension of the sprayable liquid composition typically is in the range of from about 0.1 to about 5% by weight, preferably in the range of 0.2 to 1.0% by weight. Typically, an organic material comprising a polymer:hydrophobic agent ratio in the range of from about 1:1 to about 3:1 (weight percent) will form matrices which will non-leachably retain the metallic biocide and preferentially transfer the biocide to the microorganism upon contact, as described herein. The concentration of metallic biocide is typically in the range from about 0.001 to about 20% by weight of polymer or polymer-hydrophobic agent adduct in the disinfectant solution composition.

In a preferred embodiment, a disinfecting composition according to the present invention is applied as an aerosol spray to form an antimicrobial film or layer on the surface of a substrate. In a currently preferred embodiment, the organic matrix is formed by first reacting polyhexamethylenebiguanide with an epoxy, such as methylene-bis-N,N-diglycidylaniline, to form an adduct. Stable coating solutions of the resulting adduct have been obtained in both absolute ethanol and in aqueous ethanol. The biocidal material, preferably a silver compound, is then added to the adduct solution to form a stable solution or colloidal dispersion or emulsion. The resulting mixture is diluted to the desired concentration, then is applied on the substrate surface by spraying. Spraying may be carried out, for example, using a standard trigger bottle or other conventional spray applicator, or from a pressurized aerosol can employing a suitable propellant. Such suitable propellants include nitrogen, carbon dioxide, hydrocarbon or a hydrocarbon mixture. The spray-applied liquid layer may be wiped with a cloth to spread the layer evenly on the substrate. Once applied to the substrate, the coating is allowed to dry at ambient temperature, thereby forming a polymeric film on the substrate. The resulting film is adherent, optically clear, stable to light and insoluble in aqueous solutions. The coating will not wash off with water, soap or most commercial cleaning agents. The coating can be removed, if desired, by wiping the coated surface with an alcoholic solution containing a surfactant. Examples of alcoholic solutions which can be used include ethanol, aqueous ethanol or isopropanol. Examples of surfactants which can be used include, for example, sodium lauryl sulfate or sodium dodecyl sulfate (SDS), sorbitan monolaurate, sorbitan monopalmitate, sorbitan monostearate, sorbitan sesquioleate, sorbitan trioleate, poloxyethylenesorbitan monolaurate (Tween 20), polyethylenesorbitan monopalmitate (Tween 40), polyoxyethylenesorbitan monostearate (Tween 60), polyoxyethylenesorbitan monooleate (Tween 80), polyoxyethylenesorbitan trioleate (Tween 85), or sorbitan monooleate. Ethanol solutions containing 0.01 to 5% sodium laurylsulfate, polyoxyethylenesorbitan monopalmitate or sorbitan monooleate are currently most preferred for this purpose. The applied film typically is ten microns or less in thickness, although the thickness of the coating may be varied by well-known techniques, such as increasing the solids content of the resin.

In another preferred embodiment, the disinfectant composition of the present invention may additionally contain an optical reporter that enables visual detection of presence of the composition on a substrate surface. The optical reporting material can be a compound that can be detected spectroscopically and can be a dye, flurophore, optical brightener, pH indicator or thermochromic material. Preferred optical reporter materials are optical brightening agents such as 2,2'-(2,5-Thiophenediyl)bis[5-tert-butyl-benzoxazole] (Uvitex OB) or 4,4'-bis-2-diethylamino-4-(2,5-disulphophenyl-amino)-s-triazinyl-6-amino-stilbene-2,2'-disulphonic acid, sodium salt (Tinopal) marketed by Ciba-Geigy Corporation, which can be visualized by a UV detector.

The disinfectant compositions of the present invention may be used as a hard surface disinfecting agent, e.g. as a hospital and institutional disinfectant, kitchen and bathroom disinfectant, cleaner disinfectant or floor and wall cleaner. The disinfectant compositions may also be employed as skin disinfectants, antiseptics, sanitizers, protectants, liquid wound dressings or bandages. The disinfectant compositions may be used for treating skin contacting articles, such as diapers, wound dressings, wipes, masks and surgical gowns, and non-body contacting articles, such as hospital bed rails, carpets and rugs.

The above and other objects, features and advantages of the present invention will be better understood from the following specification when read in conjunction with the accompanying drawings.

BRIEF DESCRIPTION OF THE DRAWINGS

FIG. 1A is a schematic graphic illustration of the polymer/biocide complex of the present invention, in a solvent, as applied to a surface.

FIG. 1B is a schematic graphic illustration of the polymer/biocide complex of the present invention, as applied to a surface, after evaporation of the solvent, leaving a polymer/biocide film on the surface.

FIG. 1C is a schematic graphic illustration of the contact-killing ability of the film forming matrix/biocide complex of the present invention upon contact of the film with microorganisms, wherein the polymer chains engage and disrupt the microorganism cell membrane.

FIG. 1D shows penetration of the cell membrane and transfer of the biocide from the network to proteins in the microorganism, causing cell death.

FIG. 2A is a graph illustrating the immediate (upon application) and sustained (after contacting water) disinfecting efficacy of a film formed from the composition of the invention against *S. aureus* and *E. coli.*

FIG. 2B is a graph illustrating the immediate (upon application) and sustained (after contacting water) disinfecting efficacy of a film formed from the composition of the invention against *P. aeruginosa.*

FIGS. 3A and 3B are graphs illustrating the durability of the present antimicrobial coatings after repeated cycles of challenge with *P. aeruginosa*, incubation and washing.

DETAILED DESCRIPTION

The disinfecting composition of the present invention are applied to a variety of substrates to obtain a coating or layer having antimicrobial and antiviral disinfecting action. Disinfecting compositions according to the present invention can be applied, for example, to woods, metals, paper, synthetic polymers (plastics), natural and synthetic fibers, natural and synthetic rubbers, cloth, glasses, and ceramics. Examples of synthetic polymer substrates include elastically deformable polymers which may be thermosetting or thermoplastic such as, for example, polypropylene, polyethylene, polyvinylchloride, polyethylene terephthalate, polyurethane, polyesters, rubbers such as polyisoprene or polybutadiene, polytetrafluoroethylene, polysulfone and polyethersulfone polymers or copolymers. Inorganic materials to which the present coatings can be applied include glass fiber materials, ceramics such as alumina or silica, and metals. The present antimicrobial spray also can be applied to and form a coating on sintered glass and sintered ceramic substrates.

The term "microorganism" as used herein includes bacteria, blue-green algae, fungi, yeast, mycoplasmids, protozoa and algae.

The term "biocidal" as used herein means bactericidal or bacteriostatic. The term "bactericidal" as used herein means the killing of microorganisms. The term "bacteriostatic" as used herein means inhibiting the growth of microorganisms, which can be reversible under certain conditions.

As used herein, the terms "non-leachable" and "substantially non-leachable" mean that bio-active components in films obtained by application of the disinfecting compositions do not dissolve, elute, leach or otherwise provide species into a liquid environment in contact with the said films at levels that would result in solution disinfection, that is, in antimicrobially effective amounts. Preferably, this threshold is below the minimum solution concentrations of such components to impart solution disinfection.

Organic materials useful in the present invention comprise materials which are capable of: (1) adhering to and/or forming a layer or coating on a variety of substrates, (2) reversibly binding to or complexing with the bactericide, and (3) insinuating the bactericide into the cell membrane of the microorganism. A preferred class of materials are those having the aforementioned properties, which are capable of being immobilized on a surface and which preferentially bind a biocidal metallic material in such a manner so as to permit release of the metallic biocide to the microorganism, but not to the contacting environment. Most preferred is the class of organic materials having antimicrobial properties, that is, materials which, when applied as a coating, can dissolve into, adhere to, disrupt or penetrate the lipid bilayer membrane of a microorganism in contact with the coating. In a preferred embodiment, the organic material is a polymer containing segments which, when the polymer forms a coating on a surface, are capable of engaging microorganisms which come into contact with the coating. By "engaging" is meant that the coating can attach and temporarily immobilize a microorganism in contact with it. For this purpose, surface active agents, such as cationic compounds, polycationic compounds, anionic compounds, polyanionic compounds, non-ionic compounds, polyanionic compounds or zwitterionic compounds may be used. Organic materials which currently are most preferred for use in the invention are polymeric biguanide compounds. When applied to a substrate, these polymers form a coating on the substrate which can engage and disrupt a microorganism as shown in FIG. 1.

Polymeric materials useful in the present invention include benzalkoniumchloride derivatives, α-4-[1-tris(2-hydroxyethyl) ammonium-2-butenyl ]poly[1-dimethylamnmonium-2-butenyl]-ω-tris(2-hydroxyethyl) ammonium chloride. Preferred polymeric compounds include polymeric biguanides and their salts of the general formula:

or water soluble salts, where X is any aliphatic, cycloaliphatic, aromatic, substituted aliphatic, substituted aromatic, heteroaliphatic, heterocyclic, or heteroaromatic compound, or a mixture of any of these, and $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these, where n is an integer equal to or greater than 1, and wherein Z is an anion such as $Cl^-$ or $OH^-$. The currently most preferred polymeric compound is polyhexamethylene biguanide (available from Zeneca Biocides, Inc. of Wilmington, Del. as a 20% aqueous solution under the trade name COSMOCIL-CQ).

In one embodiment of the present invention, the organic material comprises an organic material which has been reacted with a hydrophobic agent to form an adduct. Hydrophobic agents which can be used in the present invention are those which react with the organic material to form the adduct. Suitable hydrophobic agents include, for example, organic compounds containing multifunctional groups such as isocyanates, epoxides, carboxylic acids, acid chlorides, acid anhydrides, succimidyl ether aldehydes, ketones, alkyl methane sulfones, alkyl trifluoromethane sulfonates, alkyl paratoluene methane sulfones, alkyl halides and organic multifunctional epoxides. In a currently preferred embodiment, a polyhexamethylene biguanide polymer is reacted with an epoxide, such as methylene-bis-N,N-diglycidylaniline. The degree of hydrophobicity of the resulting adduct can be adjusted by choice of the hydrophobic agent. The organic material can be polymeric or non-polymeric, however the resulting adduct must be capable of forming a coherent film.

The biocidal material can be any antimicrobial material which is capable of non-leachably binding to or complexing with the organic matrix, but which, when placed in contact with the microorganism, preferentially transfers to the microorganism. For this purpose, metallic materials which are toxic to microorganisms are preferred. The metallic material can be a metal, metal oxide, metal salt, metal complex, metal alloy or mixture thereof. Metallic materials which are bactericidal or bacteriostatic and are substantially water-insoluble are preferred. By a metallic material that is bacteriostatic or bactericidal is meant a metallic material that is bacteriostatic to a microorganism, or that is bactericidal to a microorganism, or that is bactericidal to certain microorganisms and bacteriostatic to other microorganisms. Examples of such metals include, e.g., silver, zinc, cadmium, lead, mercury, antimony, gold, aluminum, copper, platinum and palladium, their oxides, salts, complexes and alloys, and mixtures of these. The appropriate metallic material is chosen based upon the ultimate use of the device. The currently preferred metallic materials are silver compounds.

Carriers useful in the present invention include liquids, gels or foams. Liquids useful as the liquid carrier for the antimicrobial materials in the present invention include any polar liquid, including water, alcohols such as ethanol or propanol, polar aprotic solvents such as N, N-dimethyl formamide (DMF), dimethyl sulfoxide (DMSO) or N-methyl-2-pyrrolidone (NMP), and mixtures thereof. The currently preferred liquid carrier comprises a mixture of ethanol and water. The liquid carrier in the present invention can itself be an antimicrobial disinfectant capable of causing immediate disinfection upon application of the formulation on a bacterially contaminated surface, including specially denatured alcohol (SD-alcohol) which is comprised of 95% ethyl alcohol denatured with 5% isopropanol, or pure isopropanol.

The biocidal material can be introduced into the matrix either contemporaneously with or after application of the organic material to a surface.

The amount and/or type of the antimicrobial composition which is used in a particular application will vary depending on several factors, including the type and amount of contamination which is likely to occur, and the size of the antimicrobial surface. The amount of antimicrobial used will be a minimum amount necessary to maintain the sterility of the surface. As stated above, this amount will vary depending upon various considerations understood by those of ordinary skill in the art.

Figure 1A:
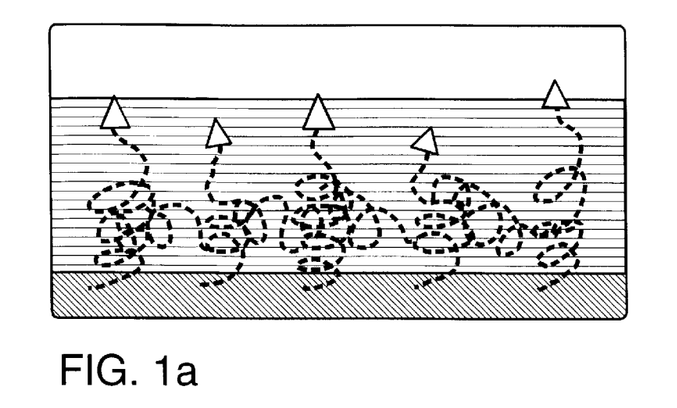
Figure 1B:
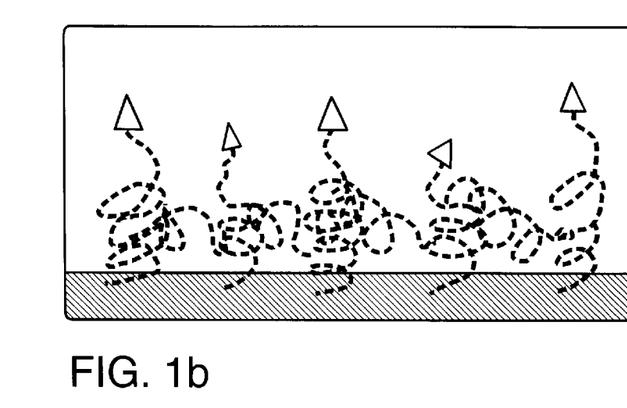
Figure 1C:
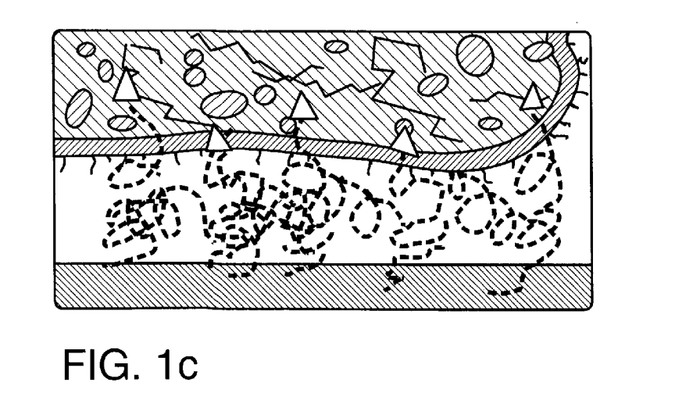
Figure 1D:
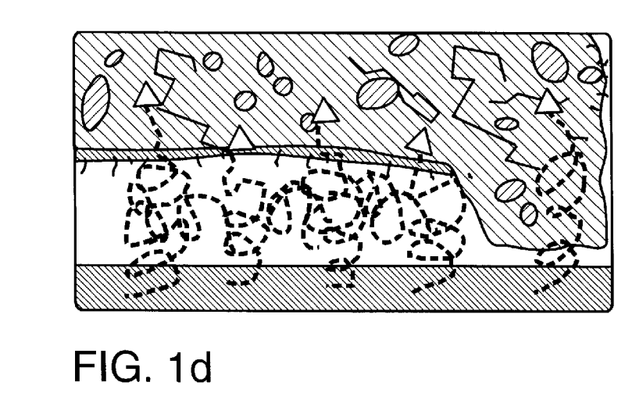
Figure 2A:
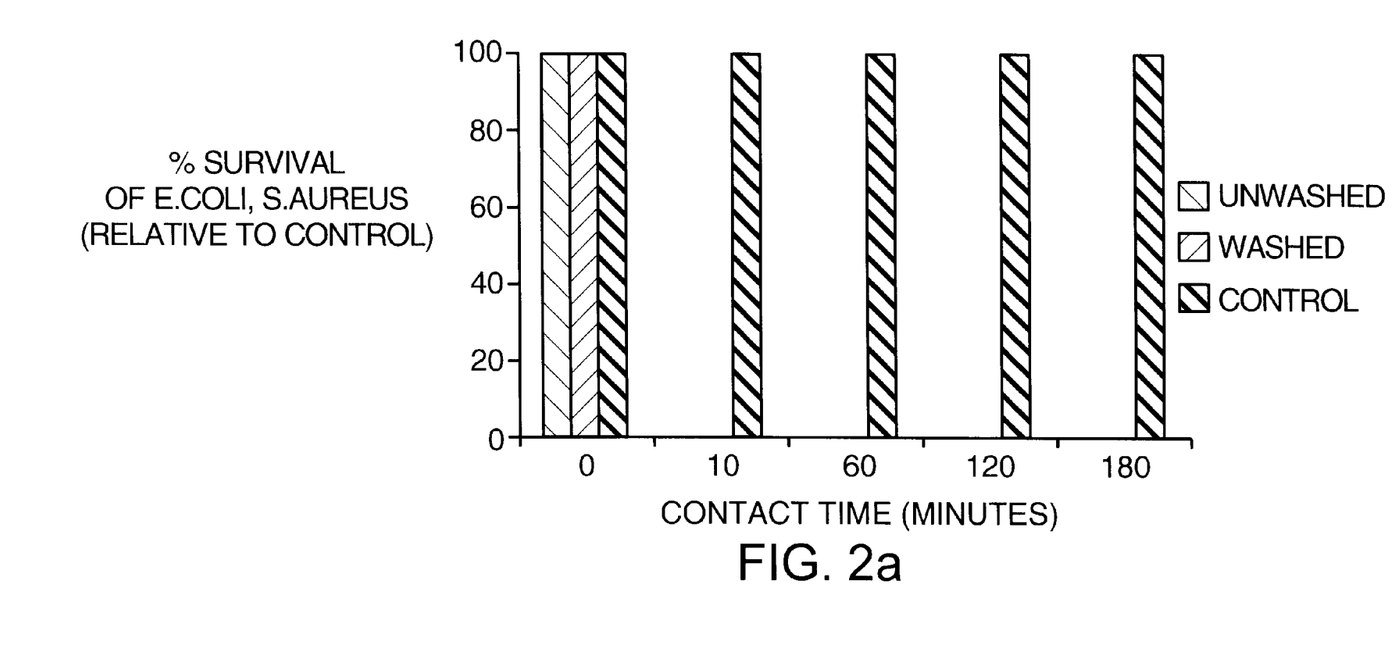
Figure 2B:
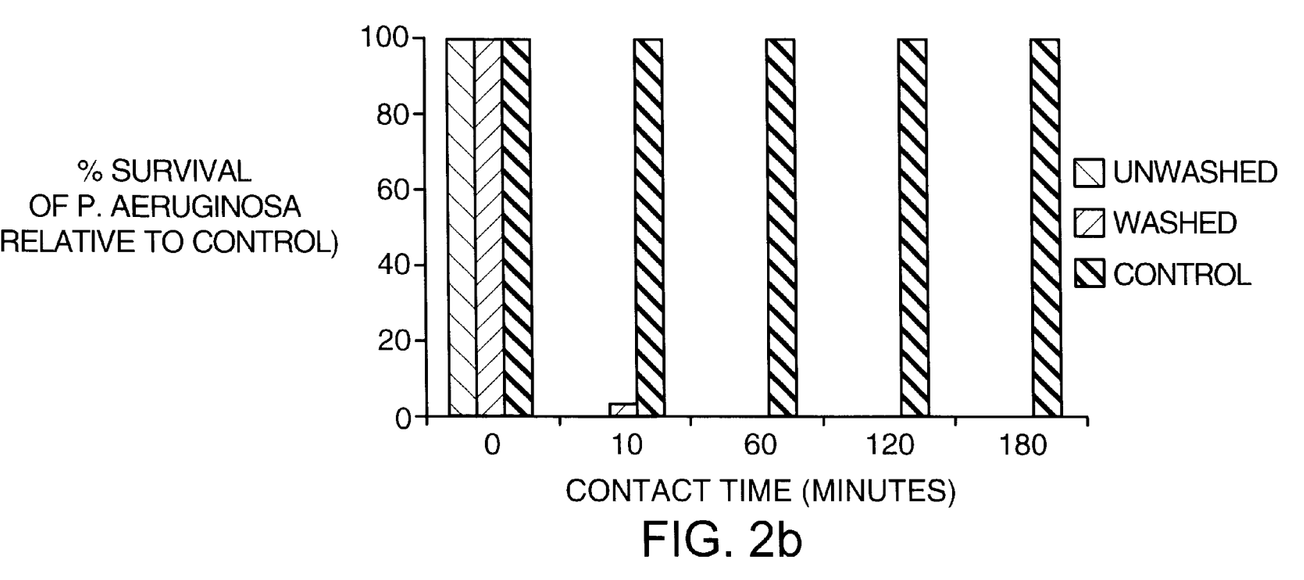

In a preferred embodiment, when the disinfectant composition is applied to a substrate, the organic material forms an insoluble, non-leachable film having a unique configuration: some of the organic material protrudes into the surrounding environment, that is, "arms" or "tentacles" of the organic material project away from the matrix and into the surrounding environment. This phenomenon can be understood by referring to FIG. 1, which is a schematic graphic illustration of a preferred embodiment of the present invention in which the organic material is a biguanide polymer reacted with a water insoluble organic compound to increase the water insolubility of the said polymer, and the biocidal metallic material is a silver halide salt, preferably silver iodide. FIG. 1A show the polymer film having tentacles projecting into the ambient environment, with the silver salt being present within reservoirs and on the tentacles. Without wishing to be bound by any theory, it is believed that when a microorganism contacts the coating, the biguanide polymer tentacles dissolve into the lipid bilayer constituting the organism cell membrane surrounding the microorganism, thereby introducing silver molecules into the interior of the microorganism or to proteins within the cell membrane. Silver has a greater binding affinity for certain proteins in the microorganism than for the polymer film, and therefore complexes with the cellular proteins and is transferred into the microorganism, thereby causing protein denaturation within the organism resulting in its death. Specifically, it is known that the silver forms complexes with the sulfhydryl and amino groups of the cellular proteins.

In this embodiment, the silver salt is attached to or impregnated into the matrix comprising the film and on the tentacles of the polymer such that the silver is substantially non-leachable into the surrounding environment, that is, substantially no silver leaches from the coating into a liquid in contact with the coating. This is substantiated by performing the standard Kirby-Bauer zone of inhibition test using test substrates which contain a disinfecting composition. The absence of a zone in such tests indicates that bioactive components from the composition do not dissolve, elute, leach or provide species in the contacting medium at levels necessary to cause death. Again, not wishing to be bound by any theory, it is believed that the silver salt forms complexes with functional groups in the polymer, and that the complexed silver resists leaching into ambient liquids or other materials (e.g. water, and aqueous solutions including common cleaning liquids) in contact with the treated surface. However, when the treated surface becomes exposed to cellular proteins, the silver preferentially complexes with the proteins.

In a currently preferred embodiment, the polymeric material is polyhexamethylene biguanide, (PHMB) and the hydrophobic agent is methylene-bis-N,N-diglycidylaniline (MBDGA). The preferred silver salt is a silver halide, most preferably, silver iodide or silver nitrate, which is readily converted to a silver halide, most preferably silver iodide. In this embodiment, the antimicrobial material is made by combining a solution of polyhexamethylene biguanide with a solution of the hydrophobic agent, and reacting the mixture under conditions sufficient to form a PHMB-MBDGA adduct. The ratio of PHMB to MBDGA preferably is in the range of from about 1:1 to 3:1 by weight. The concentration of the resulting adduct resin preferably is in the range of from about 0.5 to about 20% by weight. The biocidal material, preferably silver iodide, is added to the adduct solution to form the liquid antimicrobial composition. Silver solutions having a concentration of from about 0.005 to about 0.5% can be used for this step. Silver iodide is currently the most preferred form of the biocidal metallic material. It is added either to the adduct solution as such or obtained by adding silver nitrate to the adduct solution and converting it to silver iodide by addition of and alkali metal iodide such as sodium or potassium iodide. The silver iodide forms reservoirs in the matrix, and becomes attached to the tentacles. Silver iodide has sufficient affinity for the PHMB polymer that it forms an insoluble complex that will not leach into ambient solutions or other materials in contact with the material, even at elevated temperatures. However, when a microorganism contacts the film, the tentacles disrupt the microorganism's lipid bilayer membrane, thereby introducing the silver iodide into the microorganism. Silver iodide has greater affinity for certain proteins within the microorganism than for the PHMB-MBDGA matrix, and forms complexes with these proteins, that is, the silver is preferentially transferred from the coating to the microorganism. The silver accumulates to toxic levels in the microorganism and kills it. The silver iodide reservoirs within the matrix replenish the silver iodide on the tentacles lost to the microorganism by reestablishing the equilibrium for formation of the complex $(AgI+PHMB \leftrightarrows [PHMBAgI])$.

The present invention provides stable disinfectant compositions which can be used to apply adherent antimicrobial films or layers onto a wide range of materials, including those commonly used in membranes, medical device manufacture, hospitals, laboratories, kitchens and bathrooms. The antimicrobial films or layers are capable of providing sustained disinfection action for prolonged periods. In a preferred embodiment, the liquid composition is a sprayable formula which can be spray-applied directly to most surfaces without prior surface modification.

Surfaces treated with the disinfectant composition according to the present invention exhibit (i) immediate antimicrobial disinfection activity against both gram positive and gram negative bacteria and yeast, and are resistant to fungal growth, and (ii) instant antiviral activity. Treated surfaces completely kill organisms at challenge levels of $10^6$–$10^8$ CFU/mL within 8 to 20 hours at 30° C., depending on organism type. The treated surfaces inactivate viruses such as poliovirus, hepatitis-B and rhinovirus. Additionally, the disinfectant composition according to the present invention exhibits antimicrobial disinfection activity for prolonged periods after its application, even after being contacted with water and aqueous cleaner solutions such as soaps and shampoos.

The antimicrobial composition of the present invention can be applied to a surface to form contact-killing coatings or layers on a variety of substrates. As shown in the Examples, the material forms a non-leaching contact-killing surface on surfaces such as ceramic tiles, fiberglass or enamel, synthetic countertops, chrome fixtures, shower curtains, mirrors and other clinical or home areas where microbial contamination is a concern.

For example, surfaces in medical offices or hospitals, such as treatment tables or consoles in a typical dental office, have proven to be a major source of bacterial contamination-posing potential health risks to the patients and staff. Coating or treating these surfaces with the antimicrobial materials of the present invention can reduce or prevent microbial contamination on these substrates. In the home, surfaces in kitchens and bathrooms, including bathroom fixtures, countertops, mirrors, and accessories (e.g., shower curtains) can be treated with the present composition to reduce or eliminate microbial contamination.

The present antimicrobial materials have been tested against the bacteria most commonly found in water (see Examples below). Treated ceramic tiles withstood repeated attempts to introduce microbial contamination at very high challenge levels, while untreated control tiles developed extensive bio-films.

The present composition forms a long lasting, optically clear, non-streaking coating or layer on the surface to which it is applied. The coating can not be washed off with water, soap or most commercially available cleaning products formulated for use in the kitchen or bath. The coating can be removed by wiping the coated surface with an acidic, alkaline or alcoholic solution, for example, with aqueous ethanol, isopropanol or mixture thereof The invention is further illustrated by the following examples, which are not intended to be limiting in any way.

EXAMPLES

All examples consist of adduct resins obtained by reaction of polyhexamethylenebiguanide hydrochloride salt (PHMB.HCl) or polyhexamethylenebiguanide free base (PHMB) with bifunctional or multifunctional epoxides. Epoxides used in the present invention include methylene-bis-N,N-diglycydyl aniline (MBDGA) sold as Araldite MY-720 by Ciba Resins; bisphenol A epichlorohydrin (Average molecular weights ranging from 400 to 1700) (Aldrich Chemical Company); or N,N-diglycidyl-4-glycidyloxyaniline (Aldrich Chemical Company). The ratio of PHMB (base) or PHMB.HCl to epoxide is from about 2:1 to 1:1 (wt:wt ratio).

Example 1
Preparation of PHMB Solutions

Example 1A

To a stirred solution of 160 ml of PHMB.HCl solution (20 wt % aqueous solution sold as Cosmocil CQ by Zeneca Biocides, Wilmington, Del.), a solution containing 20 g of methylene-bis-N,N-diglycidylaniline (MBDGA) (Ciba Resins, Hawthorne, N.J.) dissolved in 100 mL N,N-dimethylformamide (DMF) and 130 mL ethanol, was added dropwise. The reaction mixture was refluxed with stirring for 1 hour during which time the initially turbid solution turned clear. The solution was allowed to cool to room temperature to give the adduct resin as a 20% wt solids. This solution was diluted appropriately with absolute alcohol.

Example 1B

To a stirred solution of 32.5 mL of PHMB base in ethanol (prepared by addition of NaOH solution to aqueous PHMB.HCL followed by filtration drying and redissolution in ethanol) containing 13% solids by weight, 32.5 g of bisphenol-A epichlorohydrin (ave. mol. wt.=1075) dissolved in 77 mL of DMF was added rapidly with stirring. The reaction mixture was refluxed with stirring for 1 hour during which time the initially turbid solution turned clear. The solution was allowed to cool to room temperature to give the adduct resin as a 20% wt solids. This solution was diluted appropriately with absolute alcohol.

Example 1C

To a stirred solution of 130 mL of PHMB.HCL solution (20 wt % aqueous solution sold as Cosmocil CQ by Zeneca Biocides) was added 70 mL of deionized water followed by a solution containing 17.3 g of N,N-diglycidyl-4-glycidyloxyaniline (Aldrich Chemical Company) dissolved in 25 mL N,N-dimethylformamide (DMF) and 130 mL ethanol was added dropwise. The reaction mixture was refluxed with stirring for 2 hours during which time the initially turbid solution turned clear. The solution was allowed to cool to room temperature to give the adduct resin as a 20% wt solids. This solution was diluted appropriately with absolute alcohol.

Example 2
Preparation of Sprayable Antimicrobial Compositions

Four different formulations were prepared:

1. Example 2A, Formulation ATT1: contained PHMB.HCL and AgI as the active ingredients; formulated as an antimicrobial coating for polar plastics, cellulosics and metals; applied from organic solvent based solutions.

2. Example 2B, Formulation ATT2: contained PHMB.HCL and AgI as the active ingredients; formulated as a general purpose antimicrobial coating; applied from aqueous ethanol based solutions.

3. Example 2C, Formulation ATT3: contained PHMB.HCL/epoxy copolymer and AgI as the active ingredients; formulated as a general purpose antimicrobial coating; applied from aqueous ethanol based solutions.

4. Example 2D, Formulation ATT4: contained PHMB.HCL/epoxy copolymer and AgI as the active ingredients; formulated as a general purpose antimicrobial coating; applied from aqueous solutions with a water content of more than 90%.

Example 2A

Formulation ATT1

20g of Cosmocil CQ (Zeneca, Biocides, Wilmington, Del.) 4 g of silver iodide (AgI) 2 g of potassium iodide (KI) and 80 ml of N,N-dimethylformamide (DMF) were mixed together in a flask for 15 minutes. The volume of obtained solution (light yellow color) was adjusted with DMF to 100 ml. The resulting solution contained 10% (w/v) of solids. Prior to application, stock solution was 10-fold diluted with 1:1 (v/v) mixture of DMF and ethanol to a final solids content of 1% (w/v).

Example 2B

Formulation ATT2

20 g of Cosmocil CQ, 2.8 g of sodium dodecyl sulfate (SDS), 1.3 g of AgI, 0.4 g of KI and 25 ml of DMF, 20 ml N-methyl-2-pyrrolidone (NMP) and 20 ml of ethanol were mixed together in a flask for 30 minutes. The volume of obtained stock solution (yellow-brown color) was adjusted with ethanol to 100 ml. Prior to application, the stock solution was diluted with 70% (v/v) aqueous ethanol to a solids content of 0.5% (w/v).

Example 2C

Formulation ATT3

20 g of Cosmocil CQ was mixed with 25 ml of DMF solution containing 5 g of Araldite 720 epoxy resin as described in Example 1A. The resulting slurry was heated to 95–98° C. After 30 minutes of agitation at this temperature, the clarified solution was cooled down and filtered.

Then 40 ml of obtained solution, 2.8 g of sodium dodecyl sulfate (SDS), 1.3 g of AgI, 0.4 g of KI, 5 ml of DMF, 20 ml of ethanol and 20 ml of NMP were mixed together in a flask for 30 minutes. The volume of obtained stock solution (yellow-brown color) was adjusted with ethanol to 100 ml. Prior to application the stock solution was diluted with 70% (v/v) aqueous ethanol to a final solids content of 0.5% (w/v).

Example 2D

Formulation ATT4

25 g of Cosmocil CQ was mixed with 25 ml of a DMF solution containing 5 g of bisphenol A epichlorhydrin epoxy resin, average molecular weight 480 (obtained from Aldrich Chemical Co., Milwaukee, Wis.) as described in Example 1B. The resulting slurry was heated to 95–98° C. After 30 minutes of agitation at this temperature, the clarified solution was cooled down and filtered.

40 ml of the obtained solution, 2 g of AgI and 0.6 g of KI, 2.5 g of polyvinyl pyrrolidone (PVP) (average MW 29000, obtained from Aldrich, Milwaukee, Wis.), 20 ml of ethanol and 20 ml of distilled water were mixed together in a flask for 30 minutes. The volume of obtained stock solution (colorless) was adjusted with water to 100 ml. Prior to application, the stock solution was diluted with deionized water to get final solids content of 0.5% (w/v).

Example 2E

Formulation S1 and S3

To 227 ml of a 12.9% PHMB-MBGDA adduct solution in ethanol was added 12.6 g of sodium lauryl sulfate (Aldrich Chemical Company, Milwaukee, Wis.) dissolved in a mixture containing 30 ml of water and 30 ml of ethanol, with agitation. To this was added 2.1 g of silver nitrate added in a mixture containing 30 ml of water and 30 ml of ethanol. The resulting solution was diluted with 542 ml of ethanol and 51 ml of N-methyl-2-pyrrolidone with agitation. This solution was combined with a solution containing 3.1 g potassium iodide in a mixture of 30 ml of water and 30 ml of ethanol. The mixture was agitated for 1 hour after which the resulting solution was filtered through 5 micron filter. The resultant emulsion is diluted as necessary to obtain the liquid disinfectant in the use concentration.

Example 3

Coating Application

The coatings described in Example 2 were applied by spraying over the surface of ceramic tiles (using a standard 22-oz trigger bottle) and spreading the liquid evenly with a soft tissue. One square foot of a tile surface was treated at once (64 tiles, each 35mm x 35 mm in size). Alcohol based formulations were dried for 10 minutes, and aqueous or DMF based formulations were dried for 30 minutes.

Antimicrobial activity testing

The coated samples were tested for antimicrobial efficacy in the following tests (results shown in Table 1):

A. Standard bactercidal test for hospital grade disinfectant;

B. Standard fungicidal test for hospital grade disinfectant;

C. Standard virucidal test for hospital grade disinfectant;

D. Residual efficacy test for disinfectant;

E. Multiple microbial challenge test for sustained residual disinfection—results shown below;

F. Antimicrobial efficacy of the coating after one exposure to common bathroom cleaning solutions—results shown in Example 8;

G. Coating antimicrobial efficacy in the presence of growth supporting media—results (not shown) indicated no growth on the coated tiles; and H. Kirby-Bauer zone of inhibition test—results (not shown) did not show a zone of inhibition, indicating that the coatings were non-leachable.

A–C. Standard tests for bacterial, viral andfungicidal activity

Tests were run with S3 formulation per American Society of Analytical Chemists (AOAC) protocols.

Formulation was applied to glass slides that were subjected to bacterial, fungal and viral challenge per standard test conditions. The formulation was disinfecting, virucidal and fungicidal under these test conditions. The efficacy data are summarized in Table 1 (1a–c).

D. Sustained residual disinfection testing

Tests were done on residual film obtained from S3 formulation on glass slides and ceramic tiles after evaporation of solvents.

The residue was immersed in water at 25° C. for 24 hours, after which it was challenged with *Psedomonas aeruginosa, Staphylococcus aureus* and *Salmonella choleraseius*. Tiles and slides containing residue after water contact were inoculated with 0.3 ml of a microorganism suspension in PBS. Incubation of microorganisms was carried out at ambient temperature (20° C.) in a humidity chamber. Planctonic microorganisms were recovered from the tile surface, then serial dilutions were performed and plate counted by standard techniques. The reduction in the microorganism count compared to control tiles is reported in Table 1d.

E. ATT coating performance in multiple microbial challenge test

Nonporous glazed tiles, 35×35 mm size, treated with the ATT formulations were tested for antimicrobial efficacy in a multiple challenge test with gram negative bacteria *Pseudomonas aeruginisa* and *Escherichia coli*; gram positive bacteria, *Staphylococcus aureus*; fungus *Aspergillus niger* (mold); and *Candida albicans* (yeast).

Tiles were repetitively inoculated with 0.3 ml of a microorganism suspension in PBS. Between the inoculations the tile samples were rinsed with tap water (250 ml per tile) and air-dried. No sterilization of the samples was performed between inoculation cycles. Incubation of microorganisms was carried out at ambient temperature (20° C.) in a humidity chamber. Planctonic microorganisms were recovered from the tile surface, then serial dilutions were performed and plate counted by standard techniques. The reduction in the microorganism count compared to control tiles is reported in Table 2.

TABLE 1

ANTIMICROBIAL EFFICACY OF DISINFECTANT FORMULATION

I. Initial Efficacy of Surfacine Disinfectant Spray

Table 1 a. Germicidal Efficacy of Disinfectant Formulation

| Claim | Batch* | Test Mode | Organism | ATCC # | Replicates w/out soil load | with soil load | Antimicrobial Time To Act | Organism Recovery cfu/sample Control | Test | Reduction Percentage | $Log_{10}$ | Remarks |
|---|---|---|---|---|---|---|---|---|---|---|---|---|
| Hospital Disinfectant | S3 × 16 | Spray | P. aeruginosa | 15442 | 30 | *40 | 10 minutes | $10^6$ | 0 | 99.9999 | 6 | 1 soil sample tested positive for presence* |
| | | | S. aureus | 6538 | 20 | 10 | 10 minutes | $10^6$ | 0 | 99.9999 | 6 | |
| | | | S. choleraesuis | 10702 | 20 | 10 | 10 minutes | $10^6$ | 0 | 99.9999 | 6 | |

*Data represents 5 batches

Table 1 b. Virucidal Efficacy of Disinfectant Formulation

| Claim | Batch | Test Mode | Virus | Type | ATCC # | Strain | Antimicrobial Time To Act | Soil Load | Replicate # | $Log_{10}$ Reduction | Remarks |
|---|---|---|---|---|---|---|---|---|---|---|---|
| Virucidal Activity | S1 × 16 | Spray | Poliovirus | 1 | VR-1000 | Brunhilde | 10 minutes | Yes | 4 | 5.5 | Complete Inactivation |
| | S1 × 16 | | Herpes Simplex Virus | 1 | VR-733 | F(1) | 10 minutes | Yes | 4 | 5 | Complete Inactivation |
| | S1 × 16 | | Rhinovirus | 37 | VR-1147 | 151-1 | 10 minutes | Yes | 4 | 4 | Complete Inactivation |
| | S3 × 16 | | Hepatitis A | | VR-1073 | HM-175 | 10 minutes | Yes | 4 | 3 | Complete Inactivation |

Table 1 c. Fungicidal Efficacy of Disinfectant Formulation

| Claim | Batch* | Test Mode | Organism | ATCC # | Replicates w/out soil load | with soil load | Antimicrobial Time To Act | Organism Recovery cfu/sample Control | Test | Reduction Percentage | $Log_{10}$ | Remarks |
|---|---|---|---|---|---|---|---|---|---|---|---|---|
| Fungicidal | S3 × 16 | Spray | Trichophyton mentagrophytes | 9533 | 0 | 10 | 10 minutes | $10^5$ | 0 | 99.999 | 5 | Complete Inactivation |

II. Sustained Residual Disinfection Efficacy of Disinfectant Formulation

Table 1 d. Sustained Residual Disinfection Efficacy of Disinfectant Formulation

| Claim | Batch | Test Mode | Organism | ATCC # | Substrate | Replicates | Antimicrobial Time To Act | Organism Recovery cfu/mL Control | Test | Reduction Percentage | $log_{10}$** |
|---|---|---|---|---|---|---|---|---|---|---|---|
| Sustained Residual Disinfection | S3 × 16 | 24 hours after spray and water contact | P. aeruginosa | 15442 | HDPE | 50 | 20 Hours | $10^6$ | 0 | 99.999 | 5 |
| | | | | 15442 | glass | 32 | 20 Hours | $10^5$ | 0 | 99.99 | 4 |
| | | | S. aureus | 6533 | glass | 3 | 20 Hours | $10^4$ | 0 | 99.9 | 4 |

Treated HDPE samples (after drying) were contacted with 14 mL/cm² of deionized water for 24 hours at room temperature (Protocol IB-M0009-H)
Treated glass slides were rinsed with 5 mL DI water/slide (Protocol IB-M009-G)
Data represents 4 batches of end use formulation.
*Attributed to non-uniform coverage of substrate surface during application procedure.
**Log reduction based on sensitivity of plating technique

TABLE 2

Antimicrobial Efficacy of Spray Coating in Repetitive Challenge Experiments Involving 10 Cycles microorganism count reduction compare to control, % reduction

| Coating | Organism | Incubation | cycle 1 | Cycle 2 | cycle 3 | Cycle 4 | cycle 5 | cycle 6 | cycle 7 | cycle 8 | cycle 9 | cycle 10 |
|---|---|---|---|---|---|---|---|---|---|---|---|---|
| ATT2 | E. coli | 20 h. RT | 99.999 | 99.997 | 99.99 | 99.997 | 99.998 | 99.999 | 99.998 | 99.999 | 99.998 | 99.997 |
| | PSA | 20 h. RT | 99.998 | 99.999 | 99.999 | 99.999 | 99.999 | 99.999 | 99.999 | 99.999 | 99.999 | 99.999 |
| | S. aureus | 20 h. RT | 99.9 | 99.97 | 98 | 60 | 99.9 | 90 | 99.9 | 99.8 | 99.96 | 99.5 |
| | C. albicans | 24 h. RT | 99.4 | 99.4 | 99.998 | 99.98 | 99.996 | 52 | 91 | 10 | | |
| | PSA* | 20 h. RT | 99.999 | 99.98 | 99.999 | 99.999 | 99.95 | 99.99 | 99.99 | 99.98 | 99.8 | 99.9 |
| ATT2 after water extraction | E. coli | 20 h. RT | 99.999 | 99.997 | 89.999 | 99.997 | 89.998 | 99.999 | 99.99 | 99.9 | 99.998 | 99.997 |
| | PSA | 20 h. RT | 99.998 | 99.999 | 99.999 | 99.999 | 99.999 | 99.999 | 99.999 | 99.999 | 99.998 | 99.999 |
| | S. aureus | 20 h. RT | 99.95 | 99.97 | 99.8 | 90 | 89 | 67 | 99.95 | 99.8 | 99.95 | 99.8 |
| | C. albicans | 20 h. RT | 99.994 | 99.8 | 97 | 99 | 60 | 77 | 77 | 0 | | |

TABLE 2-continued

Antimicrobial Efficacy of Spray Coating in Repetitive Challenge Experiments Involving 10 Cycles microorganism count reduction compare to control, % reduction

| Coating | Organism | Incubation | cycle 1 | Cycle 2 | cycle 3 | Cycle 4 | cycle 5 | cycle 6 | cycle 7 | cycle 8 | cycle 9 | cycle 10 |
|---|---|---|---|---|---|---|---|---|---|---|---|---|
| ATT4 after water extraction | E. coli PSA S. aureus C. albicans | 20 h. RT 20 h. RT | 99.997 99.997 | 99.99 99.99 | 99.99 99.99 | 99.99 99.99 | 99.99 99.998 | 99.993 99.998 | 99.8 99.6 | 99.992 99.998 | 96 92 | 91 83 |

Example 4
Contact Test for Biocidal Activity

Ceramic tiles were spray-coated with the composition described in Example 2B according to the procedure described in Example 3.

The surface biocidal activity was tested according to the following procedure:

Cultures were prepared of the following microorganisms:

*Escherichia coli* (ATCC #8739)

*Pseudomonas aeruginosa* (ATCC #9027)

*Salmonella cholerasius* (ATCC #10708)

*Staphylococcus aureus* (ATCC #6538)

*Candida albicans* (ATCC #9642)

*Aspergillus niger* (ATCC #9027)

Inoculi were prepared from cultures of these microorganisms according to known procedures. To test the antimicrobial efficacy of the present coatings, ceramic tiles treated with the coatings and untreated control tiles were sprayed with $10^6$ cfu/ml (cfu=colony forming units) of each of the above organisms. The tiles were incubated for 20 hours in a 25° C. humidity chamber. The number of viable organisms on the surface then was determined by swabbing the surfaces of the tiles and culturing the organisms collected from the surface by the spread plate method. The presence of the two fungus samples (Candida and *A. niger*) also were determined by the turbidity method on PBS extracted swabs. The control tiles showed $10^4$ to $10^6$ cfu/ml. The treated tiles showed no viable organisms.

Example 5
Efficacy After Exposure to Water

The ceramic tiles coated with the composition described in Example 4 were further tested to determine antimicrobial efficacy after washing. To simulate long-term use, the tiles were washed with tap water for 2 hours. (total volume, 1 gal/in$^2$). The biocidal and antifungal challenge tests described in Example 4 were repeated. After incubation for 20 to 72 hours, the control tiles showed $10^4$ to $10^6$ cfu/ml bacterial counts and $10^5$ to $10^6$ cfu/ml mold counts. Tiles coated with the composition of the invention showed no viable organisms.

Example 6
Kinetics of Bactericidal Activity

Figure 3A:
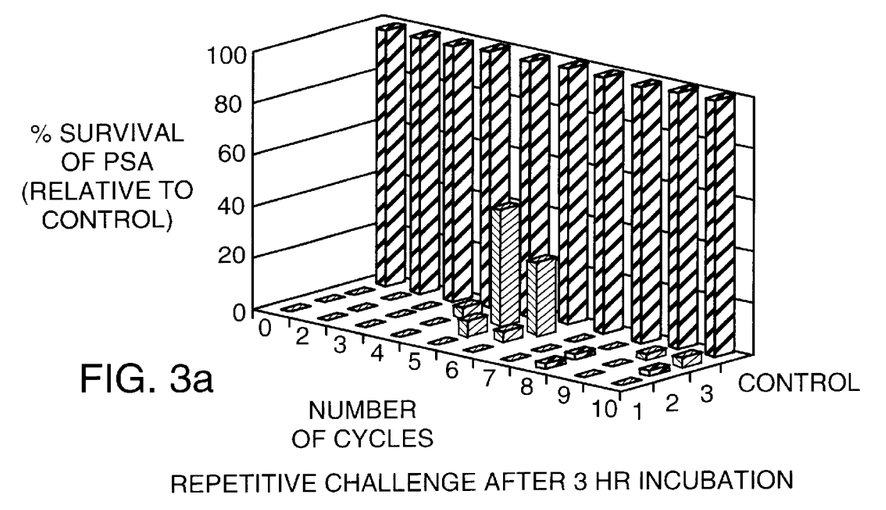
Figure 3B:
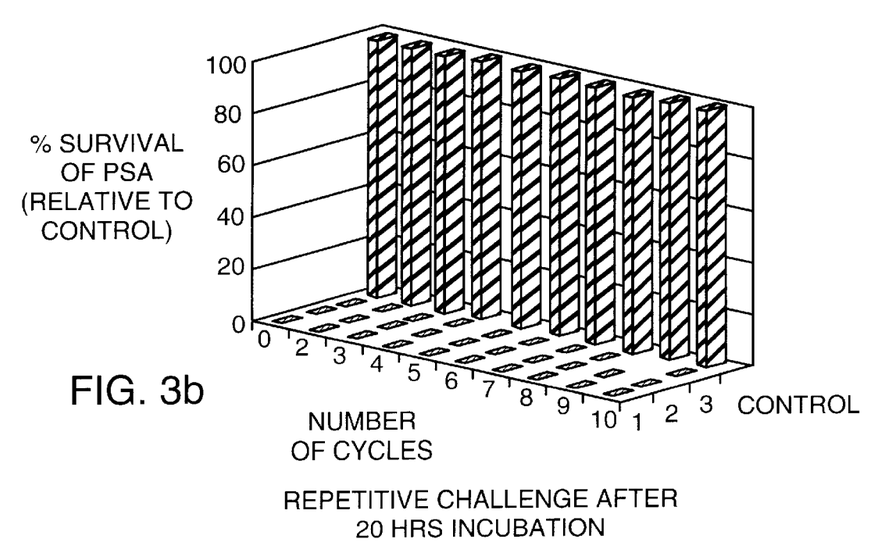

Ceramic tiles were sprayed with the compositions described in Example 2 according to the procedures described in Example 3. Some of the sprayed tiles and unsprayed controls were placed under running tap water for 2 hours (total volume, 1 gal/in$^2$) of the following organisms: *P. aeruginosa, S. aureus* and *E. coli*. The tiles were incubated at ambient temperatures, and the number of viable organisms was determined quantifiably by the spread plate method at different time points. The pre- and post-washed spray antimicrobial efficacy was determined as a function of time. The results, illustrated in FIGS. 3A and 3B, show that the treated tiles completely eliminated microorganisms from the surface within 10 minutes, whereas the untreated tiles showed no reduction.

Example 7
Efficacy After Repetitive Challenge

Ceramic tiles sprayed with the coating as described in Example 6 and untreated control tiles were challenged with $10^5$ cfu/ml *P. aeruginosa*. The tiles were incubated at 30° C. for 3 hours or for 20 hours in a humidity chamber, after which the presence of viable organisms was determined by the spread plate method. The tiles were rinsed with water (250 ml/tile) and the bacterial challenge was repeated. This cycle was repeated to obtain a total of 10 challenges each for the 3 hour and 20 hour incubations. The results, illustrated in FIGS. 4A and 4B, show that even after 10 repeated washes and bacterial challenges, the tiles treated with the present composition were free of microbial contamination.

Example 8
Efficacy of Antimicrobial Coating After Exposure to Cleaning Agents Ceramic tiles were sprayed with the coating described in Example 2B according to the procedure described in Example 3. The coated tiles (indicated in Table 2 below as "Treated") and unsprayed control tiles were exposed to various cleaning agents for 2 minutes, rinsed with 100 ml of tap water and air dried. The tiles then were inoculated with $10^6$ cfu/ml of *P. aeruginosa*, and incubated for 20 hours at 30° C. in a humidity chamber, then tested for the presence of microbes. The results, shown in Table 2 below, indicated that the cleaning agents did not affect the antimicrobial efficacy of the coating.

TABLE 2

| Cleaning Agent | Control Tiles (cfu/mL) | Treated Tiles |
|---|---|---|
| No cleaning agent | $7.70 \times 10^5$ | 0 |
| Soap | $2.80 \times 10^6$ | 0 |
| Shampoo | $2.20 \times 10^7$ | 0 |
| Alconox Detergent | $3.00 \times 10^7$ | 0 |
| All purpose Cleaning Solution | $1.00 \times 10^6$ | 0 |
| Lysol Bathroom Cleaner | $8.10 \times 10^5$ | 0 |

Example 9
Alcohol based disinfectant spray formulation incorporating modified biguanide The preparation of alcohol based disinfectant formulation was carried out in three steps.

1. Preparation of Poly(hexamethylene) biguanide (PHMB)-Epoxide (Ep) resin

2. Preparation of spray concentrate.

3. Preparation of disinfectant spray.

Step 1: Preparation of PHMB-Ep resin:

The PHMB-Ep resin was prepared as described in Example 1A.

Step 2: Preparation of spray concentrate:

Spray concentrate was prepared as follows:

| Component | Amount, in grams |
|---|---|
| BG-Ep resin | 465.0 |
| Sodium dodecyl sulfate (SDS) | 31.48 |
| Silver nitrate (AgNO$_3$) | 5.24 |
| Potassium iodide (KI) | 7.90 |
| 1-Methyl-2-pyrrodilinone (NMP) | 122.00 |
| Water | 210.70 |
| Ethanol | 1158.72 |

The BG-Ep resin was put in a 4-liter Erlenmeyer flask. Aqueous alcoholic solutions of SDS, KI and AgNO$_3$ and NMP were introduced with stirring. The entire solution was allowed to stir for a period of 2 hours to ensure uniform mixing and then filtered through a Whatman #4 filter paper and stored in appropriate package.

Step 3: Preparation of disinfectant spray:

Disinfectant spray was prepared as follows:

| Component | Amount, in grams |
|---|---|
| Ethanol | 1480.61 |
| Water | 393.58 |
| Spray Concentrate (from Step 2) | 126.36 |

To a four liter Erlenmeyer flask 1480.5 g of ethanol and 393.5 g of water was added. The solution was allowed to mix for at least 10 minutes prior to the addition of spray concentrate. The spray concentrate was added dropwise over a period of 20–25 minutes with vigorous agitation. After completion of addition, the solution was stirred for one hour at the same rate and room temperature. After which the solution was filtered through a Whatman #4 filter paper and stored appropriately.

Example 10

Alcohol based disinfectant spray formulation incorporating modified biguanide

An alternative method of preparation of alcohol based disinfectant formulation was performed involving two steps without passing through a spray concentrate step.

1. Preparation of Poly(hexamethylene) biguanide (PHMB)-Epoxide (Ep) resin.
2. Preparation of disinfectant spray.

Step 1: Preparation of PHMB-Ep resin:

The PHMB-Ep resin was prepared as described in Example 1A.

Step 2: Preparation of spray formulation:

Spray formulation was prepared as follows:

| Component | Amount, in grams |
|---|---|
| BG-Bp resin | 14.651 |
| Sodium dodecyl sulfate (SDS) | 0.828 |
| Silver nitrate (AgNO$_3$) | 0.138 |
| Potassium iodide (KI) | 0.207 |
| 1-Methyl-2-pyrrolidinone (NMP) | 3.856 |
| Water | 203.416 |
| Ethanol | 776.903 |

The BG-Ep resin was put taken in 4-liter Erlenmeyer flask. Aqueous alcoholic solutions of NMP, SDS, KI and AgNO$_3$ were added with uniform stirring. The entire solution was allowed to stir for a period of 2 hours to ensure uniform mixing and then filtered through a Whatman #4 filter paper and stored in appropriate package.

Example 11

Alcohol based disinfectant spray formulation involving unmodified biguanide:

The preparation of alcohol based disinfectant formulation was done in two steps.

1. Preparation of spray concentrate involving Poly (hexamethylene) biguanide (PHMB).
2. Preparation of disinfectant spray.

Step 1: Preparation of spray concentrate:

Spray concentrate was prepared as follows:

| Component | Amount, in grams |
|---|---|
| Cosmocil CQ | 800.0 |
| Sodium dodecyl sulfate (SDS) | 105.12 |
| Silver iodide (AgI) | 17.12 |
| Potassium iodide (KI) | 60.48 |
| 1-Methyl-2-pyrrolidinone (NMP) | 120.0 |
| Ethanol | 1040.0 |
| Water | 288.0 |

The Cosmocil CQ was put in 4-liter Erlenineyer flask. Aqueous alcoholic solutions of SDS, AgI, KI and NMP were introduced into the solution with constant stirring. The entire solution was allowed to stir for a period of 2 hours to ensure uniform mixing and then filtered through a Whatman #4 filter paper and stored in appropriate package.

Step 2: Preparation of disinfectant spray:

Disinfectant spray was prepared as follows:

| Component | Amount, in grams |
|---|---|
| Ethanol | 1850.58 |
| Water | 491.93 |
| Spray Concentrate (from Step 1) | 157.5 |

To a four liter Erlenmeyer flask, the required amounts of ethanol and water were added. The solution was allowed to mix for at least 10 minutes prior to the addition of spray concentrate. The spray concentrate was added dropwise over a period of 20–25 minutes with vigorous agitation. After completion of addition the solution was stirred for one hour at the same rate and room temperature. The solution was then filtered through a Whatman #4 filter paper and stored appropriately.

Equivalents

Those skilled in the art will be able to ascertain, using no more than routine experimentation, many equivalents of the specific embodiments of the invention described herein. These and all other equivalents are intended to be encompassed by the following claims.

What is claimed is:

1. A disinfectant composition comprising
a film-forming antimicrobial material,
an antimicrobial metallic material, and
a carrier,
wherein said composition, when applied to a surface, forms a non-permanent, adherent, water-insoluble film,
wherein said metallic material is non-leachably bound to or associated with the film,
wherein said film does not elute antimicrobial materials into contacting water at levels capable of inparting disinfecting action to said water, and
wherein said film is removable by treatment with an alcohol solution.

2. The disinfectant composition of claim 1 wherein said carrier is a liquid.

3. The disinfectant composition of claim 1 wherein the alcohol solution further comprises a surfactant an emulsifier or a detergent.

4. The disinfectant composition of claim 1 wherein the film-forming antimicrobial material is an organic polymer.

5. The disinfectant composition of claim 4 wherein the organic polymer is a polymeric biguanide material.

6. The disinfectant composition of claim 1 wherein the antimicrobial metallic material is substantially water insoluble.

7. The disinfectant composition of claim 6 wherein said antimicrobial metallic material is selected from the group consisting of a metal, metal salt, metal complex, a metal alloy, and combinations thereof.

8. The disinfectant composition of claim 7 wherein said metal is silver.

9. The disinfectant composition of claim 7 wherein the metallic material is silver nitrate or silver iodide.

10. The disinfectant composition of claim 5 wherein the polymeric biguanide material comprises polyhexamethylene biguanide or derivatives thereof.

11. The disinfectant composition of claim 5 wherein the polymeric biguanide material comprises an adduct obtained by reacting said biguanide material with a water-insoluble organic compound.

12. The disinfectant composition of claim 11 wherein the water-insoluble organic compound is selected from the group consisting of epoxide compounds, isocyanate compounds, carboxylic acid compounds, acid chloride compounds, acid anhydride compounds, succimidyl ethers, aldehydes, ketones, alkyl methanesulfonates, alkyl trifluoromethanesulfonate compounds, alkyl para-toluenemethanesulfonate compounds and alkyl halide compounds.

13. The disinfectant composition of claim 12 wherein the water-insoluble organic compound is an epoxide compound selected from the group consisting of methylene-bis-N,N-diglycidylaniline, bisphenol-A-epichlorohydrin and N,N-diglycidyl-4-glycidyloxyaniline.

14. The disinfectant composition of claim 1 further comprising an optical reporter that enables visual detection of the presence of said film.

15. The disinfectant composition of claim 14 wherein said optical reporter is selected from the group consisting of a dye and an indicator.

16. The disinfectant composition of claim 15 wherein said indicator comprises a pH indicator.

17. The disinfectant composition of claim 15 wherein said indicator comprises a thermochromic material.

18. The disinfectant composition of claim 14 wherein said optical reporter comprises an optical brightening agent.

19. The disinfectant composition of claim 14 wherein said optical reporter comprises a fluorophore.

20. The disinfectant composition of claim 19 wherein said optical reporter is selected from the group consisting of 2,2'-(2,5-Thiophenediyl)bis[5-tert-butylbenzoxazole] or 4,4'-bis-2-diethylamino-4-(2,5-disulphophenyl-amino)-s-triazinyl-6-amino-stilbene-2,2 '-disulphonic acid, sodium salt.

21. The disinfectant composition of claim 1 further comprising a surfactant, emulsifier, antioxidant or stabilizer.

22. The disinfectant composition of claim 21 wherein said surfactant is selected from the group consisting of sodium dodecyl sulfate sorbitan monooleate, sorbitan monolaurate, sorbitan monopalmitate, sorbitan monostearate, sorbitan sesquioleate, sorbitan trioleate, polyoxyethylenesorbitan monolaurate, polyoxmethylenesorbitan mononpalmitate, polyoxetylenesorbitan monostearate, polyoxyetylenesorbitan monooleate or polyoxyetbylenesorbitan trioleate.

23. The disinfectant composition of claim 2 wherein the liquid carrier comprises water, an organic solvent, mixture of organic solvents or a combination of an organic and an aqueous solvent.

24. The disinfectant composition of claim 23 wherein said organic solvent is an antimicrobial disinfectant.

25. The disinfectant composition of claim 23 wherein the liquid carrier is an alkanol or an aqueous alkanol mixture.

26. The disinfectant composition of claim 25 wherein the alkanol is ethanol or isopropanol.

27. A method for providing an antimicrobial layer on a substrate, said method comprising:
applying the disinfectant composition of claim 1 to said substrate to form an adherent, water insoluble layer or film on said substrate.

28. The method of claim 27 wherein said disinfectant composition is applied to said substrate by spraying from a spray applicator.

29. The method of claim 27 wherein said disinfectant composition is applied to said substrate by wiping, brushing or dipping.

30. The method of claim 27 wherein said disinfectant composition is applied to said substrate as an aerosol spray using a suitable propellant.

31. The method of claim 30 wherein the propellent is nitrogen, carbon dioxide or a hydrycarbon or a hydrocarbon mixture.

32. A hard surface disinfecting agent comprising the disinfectant composition of claim 1.

33. The hard surface disinfecting agent of claim 32 wherein said hard surface disinfecting agent is selected from the group consisting of hospital and institutional disinfectants, kitchen and bathroom disinfectants, cleaner disinfectants or floor and wall cleaners.

34. A skin disinfectant, an antiseptic, a sanitizer or a protectant comprising the disinfectant composition of claim 1.

35. The method of claim 27, wherein the substrate is a skin-contacting device or article.

36. The method of claim 34 wherein said skin-contacting device is selected from the group consisting of diapers, wound dressings, wipes, masks and surgical gowns.

37. The method of claim 27, wherein the substrate is a non-body contacting device or article.

38. The method of claim 37 wherein said non-body contacting article is selected from the group consisting of hospital bed rails, carpets and rugs.

* * * * *